(12) United States Patent
Gouchtchina et al.

(10) Patent No.: US 10,252,283 B2
(45) Date of Patent: Apr. 9, 2019

(54) DERMAL SPRAY APPARATUS AND METHOD

(71) Applicants: Yoanna Gouchtchina, Allen, TX (US); Enrique Gallar, Berlin (DE)

(72) Inventors: Yoanna Gouchtchina, Allen, TX (US); Enrique Gallar, Berlin (DE)

(73) Assignee: Yoanna Gouchtchina, Allen, TX (US)

( * ) Notice: Subject to any disclaimer, the term of this patent is extended or adjusted under 35 U.S.C. 154(b) by 220 days.

(21) Appl. No.: 15/651,566

(22) Filed: Jul. 17, 2017

(65) Prior Publication Data
US 2019/0015856 A1    Jan. 17, 2019

(51) Int. Cl.
| | | |
|---|---|---|
| *B05B 7/24* | (2006.01) | |
| *A61M 11/00* | (2006.01) | |
| *A45D 34/04* | (2006.01) | |
| *A45D 34/00* | (2006.01) | |

(52) U.S. Cl.
CPC ............ *B05B 7/2408* (2013.01); *A45D 34/04* (2013.01); *A61M 11/006* (2014.02); *B05B 7/2416* (2013.01); *A45D 2034/005* (2013.01); *A61M 2205/6054* (2013.01); *A61M 2205/6072* (2013.01); *A61M 2205/8206* (2013.01)

(58) Field of Classification Search
CPC .. B05B 7/2408; B05B 7/2416; A61M 11/006; A61M 2205/6054; A61M 2205/6072; A45D 34/04; A45D 2034/005
USPC ........................................................... 239/8
See application file for complete search history.

(56) References Cited

U.S. PATENT DOCUMENTS

| | | | |
|---|---|---|---|
| 5,326,062 A | 7/1994 | Remmers | |
| 5,598,808 A | 2/1997 | Wilson | |
| 6,125,844 A * | 10/2000 | Samiotes | .......... A61M 15/0065 |
| | | | 128/200.12 |
| 6,326,062 B1 | 12/2001 | Noakes | |
| 6,598,808 B1 | 7/2003 | Garcia et al. | |
| 7,225,807 B2 * | 6/2007 | Papania | ............... A61M 11/005 |
| | | | 128/200.14 |
| 7,661,563 B2 | 2/2010 | De Lataulade | |

(Continued)

FOREIGN PATENT DOCUMENTS

| | | |
|---|---|---|
| CN | 2930731 A1 | 8/2007 |
| CN | 2930731 U | 8/2007 |

(Continued)

*Primary Examiner* — Chee-Chong Lee
(74) *Attorney, Agent, or Firm* — Hoban Law Group; Kevin H. Hoban (57) ABSTRACT

A system and method for dermal spraying includes a portable, hand-held skin care device with disposable formulation capsules that spray a formulation unto the skin. The device is set to maximize absorption and provide professional and uniform quality of application. The device receives, clamps and identifies the formulation capsules and its contents. Control circuitry regulates the formulation delivery. This assures the quantity, proportion, speed and timing of the application of the cosmetic formulation, including self-cleaning cycle operation and single button control logic. The capsule enables convenience and sterility from use of disposable capsules at home. Preferably the capsules contain a cosmetic or cosmeceutical formulation. The capsule has a sealed body having any of a variety of suitable shapes such as the general shape of a cylinder with two ends having hemispherical caps.

3 Claims, 10 Drawing Sheets

(56) References Cited

U.S. PATENT DOCUMENTS

| | | | |
|---|---|---|---|
| 7,959,597 B2* | 6/2011 | Baker | A61M 1/0058 |
| | | | 604/28 |
| 8,443,799 B2* | 5/2013 | Yamashita | A61K 9/0073 |
| | | | 128/203.12 |
| 8,584,971 B2 | 11/2013 | Seabase et al. | |
| 2003/0084914 A1 | 5/2003 | Simon | |
| 2003/0157183 A1 | 8/2003 | Perrut | |
| 2004/0050964 A1 | 3/2004 | Wong et al. | |
| 2005/0054991 A1 | 3/2005 | Tobyn et al. | |
| 2006/0124662 A1 | 6/2006 | Reynolds et al. | |
| 2006/0127425 A1 | 6/2006 | Walls | |
| 2009/0039177 A1 | 2/2009 | Le Bourhis | |
| 2009/0206174 A1 | 8/2009 | Arnaud et al. | |
| 2011/0106021 A1* | 5/2011 | Ruegg | A61K 8/64 |
| | | | 604/290 |
| 2011/0118694 A1* | 5/2011 | Yodfat | G06F 19/00 |
| | | | 604/500 |
| 2011/0248052 A1 | 10/2011 | Kelly | |
| 2013/0092285 A1 | 4/2013 | Feriani et al. | |
| 2013/0245604 A1* | 9/2013 | Kouyoumjian | A61M 5/1408 |
| | | | 604/506 |
| 2013/0296807 A1* | 11/2013 | Lintern | A61J 1/20 |
| | | | 604/272 |
| 2015/0021364 A1 | 1/2015 | Zehnder et al. | |
| 2015/0201791 A1* | 7/2015 | Tinkler | B65D 85/8043 |
| | | | 426/431 |
| 2015/0335586 A1 | 11/2015 | Baruzzi et al. | |
| 2017/0051480 A1 | 2/2017 | Farcet et al. | |
| 2017/0151362 A1 | 6/2017 | Edwards et al. | |

FOREIGN PATENT DOCUMENTS

| | | |
|---|---|---|
| CN | 206228711 A1 | 6/2017 |
| EP | 2123318 A1 | 11/2009 |
| EP | 2308603 A1 | 4/2011 |
| EP | 2433656 A1 | 3/2012 |
| JP | 2006198201 A | 8/2006 |
| KR | 20120108252 A | 10/2012 |
| KR | 20120108252 A1 | 10/2012 |
| KR | 20120132067 A | 12/2012 |
| KR | 20130130569 A | 12/2013 |
| KR | 20130130569 A1 | 12/2013 |
| WO | 2015191014 A1 | 12/2015 |
| WO | 2016046385 A1 | 3/2016 |
| WO | 2017080685 A1 | 5/2017 |

* cited by examiner

DERMAL SPRAY APPARATUS AND METHOD

FIELD OF THE INVENTION

This invention relates to dermal spraying devices, and particularly to dermal spraying devices including a removable capsule.

BACKGROUND OF THE INVENTION

Skin care is very important. Many are turning to plant based and natural remedies. Certain plant-derived constituents can protect skin from deleterious effects, carcinogens, and a variety of chemical interactions. This concept has much scientific backing.

Human skin includes the epidermis, dermis and subcutis. The epidermis includes the stratum corneum and an underlying pigment layer. The stratum corneum is the outer layer of skin that protects the body. It is composed primarily of layers of dead, flattened keratinocytes surrounded by a phospholipid matrix. This acts in a similar as brick and mortar wall and functions to provide barrier to a microbial parasites as well as environmental toxins. The stratum corneum also presents a significant barrier to the delivery of transdermal drugs, vitamins, minerals, nutraceuticals and cosmeceuticals.

There are two major transdermal pathways. One is the intercellular route, which includes the movement of topically applied product around the cells of the stratum corneum via a phospholipid matrix that surrounds the cells. This is a tortuous path, so there are challenges to optimizing the speed of delivery and efficacy of skin-improving substances.

The other pathway is the transcellular pathway, which includes skin-improving substances directly passing through the cytoplasm of the dead keratinocytes of the stratum corneum, as well as the phospholipids matrix surrounding the cells. This is a more direct pathway yet there are still many challenges.

In either case, spraying a formulated fluid at a controlled pressure, spray pattern, and flow rate way can enhance penetration through the stratum corneum, so that the beneficial substances in the formulated fluid can penetrate and nourish the dermis, and in some cases enter the vasculature directly through the skin.

In the case of cosmetics and cosmeceuticals, the spray pattern, flow rate and other delivery aspects can be adjusted to optimize delivery to a desired region of the skin. For example, certain cosmetics can be delivered to provide a uniform coating on top of the stratum corneum, certain pigmentation products may be designed to reach the pigment layer under the stratum corneum.

U.S. Pat. No. 8,091,803 to Fedorov discloses a spraying device having a removable spray nozzle unit. A front end of the spraying device has a predefined cavity that receives and operatively connects with the spray nozzle unit. The device includes a liquid storage tank and a connector to a pressurized gas source. The pressurized gas passes the liquid storage tank and creates a low pressure region that utilizes the Venturi Effect to pull liquid out of the liquid storage tank. The tank has a removable cover to enable refilling of the liquid.

While the Fedorov invention represents advancement in the art, maintaining a connection to pressurized air source limits the use of the device to those that have compressed air available. Most consumers, while having a myriad of gadgets in their dressing room, lack a compressed air source. Further, refilling a liquid storage tank may result in spillage.

U.S. Pat. No. 8,074,899 to Mehta includes an airbrush delivery system having gravity feed cup, which extends from the airbrush device. The feed cup is cone shaped for easily delivering liquid to the air brush. The air brush system includes a compressed air source attached to the air brush device. The cone shaped cup apparently funnels liquid into the air brush. While the cone shape has one enlarged end to apparently inhibit spillage, a user may find that a rapid change in orientation of the air brush could challenge the ability of the cone shaped feed cup to confine the liquid.

What is desired is a way to bring the convenience of an air brush to the public in a way that is convenient and not messy.

SUMMARY OF THE INVENTION

The present invention includes an improved way of delivering transdermal cosmeceuticals and nutraceuticals to the skin of a subject. The cosmeceuticals and transdermal nutraceuticals are preferably formulated fluids including essential oils or plant extracts and excipients that are non-toxic. While the present invention is focused on delivering transdermal nutraceuticals and cosmeceuticals, it is possible to adapt the inventive concept for makeup, skin pigmentation, sunscreen, body art paint, air brush tattoos and other dermally applied substances. The formulated fluids are encapsulated in a capsule, or ampoule. In one embodiment, the formulated fluid is formulated for skin care.

The invention includes a dermal spray device having a body enclosing a battery, a pump and control electronics operatively connecting the battery and the pump. A spray head including a spray nozzle attaches to the body and defines a compartment for receiving a capsule containing fluid.

A first needle attaches within the compartment. The needle is a hollow bore needle configured to pierce a capsule during insertion into the compartment, or after the capsule is inserted into the compartment. The first needle communicates with the pump to deliver pressurized or compressed air to the capsule.

A second needle attaches within the compartment to pierce the capsule in the compartment. The second communicates with the nozzle to enable the spray device to spray formulated fluid from the capsule to the skin of a subject.

A door mounts on body to selectively open and close the compartment. The door enables rapid insertion and removal of a capsule into and out from the compartment, respectively.

When a capsule inserts into the compartment, and the door closes, the needles pierce the capsule and the pump pressurizes the inserted capsule to spray the fluid through the nozzle. The formulated fluid has a viscosity of between that of water, which is approximately 1 centipoise, and less than latex house paint, which is approximately 1500 centipoise, for reference. Preferably, the formulated fluid has a viscosity of between 200-1200 centipoise. The viscosity values herein are characteristic of a temperature of 25° C.

In one embodiment, closing of the door mechanically presses the capsule against the needles to effectuate piercing. In another embodiment, closing the door enables the needles are automated to move axially and thereby pierce the capsule when it is properly positioned in the compartment. Preferably, the pump produces a nozzle pressure of between 2-25 pounds per square inch (PSI), and more preferably a pressure of between 2-15 PSI. The nozzle preferably has an opening diameter of between 0.2 mm to 0.3 mm to optimize delivery of a formulated fluid at between 2-15 PSI. In alternate embodiments, more than one nozzle, or nozzle opening, are utilized.

Alternate embodiments rely on a varied mechanical architecture of the dermal spray device. In particular, the spray device is designed having vent needle (upper needle) to enable ambient air to enter or exit the capsule while the second (lower) needle draws formulated fluid out from the capsule using the Venturi Effect. In particular, when the pump drives air through the nozzle this air flow creates a negative pressure to draw formulated fluid from the capsule, via the lower needle, and into the air flow that is directed out through the nozzle by the pump.

A method of the present invention includes providing a spray device that is portable. The spray device is designed and contoured to be hand held. The spray device includes a door that encloses a compartment capable of holding a capsule having machine readable indicia.

The method includes the step of first opening the door and inserting a capsule into the compartment, next closing the door and piercing the capsule to enable delivery of the formulated fluid, and automatically reading the machine readable indicia. Reading the machine readable indicia enables the present invention to automatically determine spray parameters based on the contents of the capsule. For example, the spray parameters may include desired system pressure and fluid flow rates.

The method determines a desired a capsule pressure from the machine readable indicia and pressurizes the capsule to the determined capsule pressure. At the determined pressure the method sprays the formulated fluid onto the skin of a subject.

DETAILED DESCRIPTION

Figure 1:
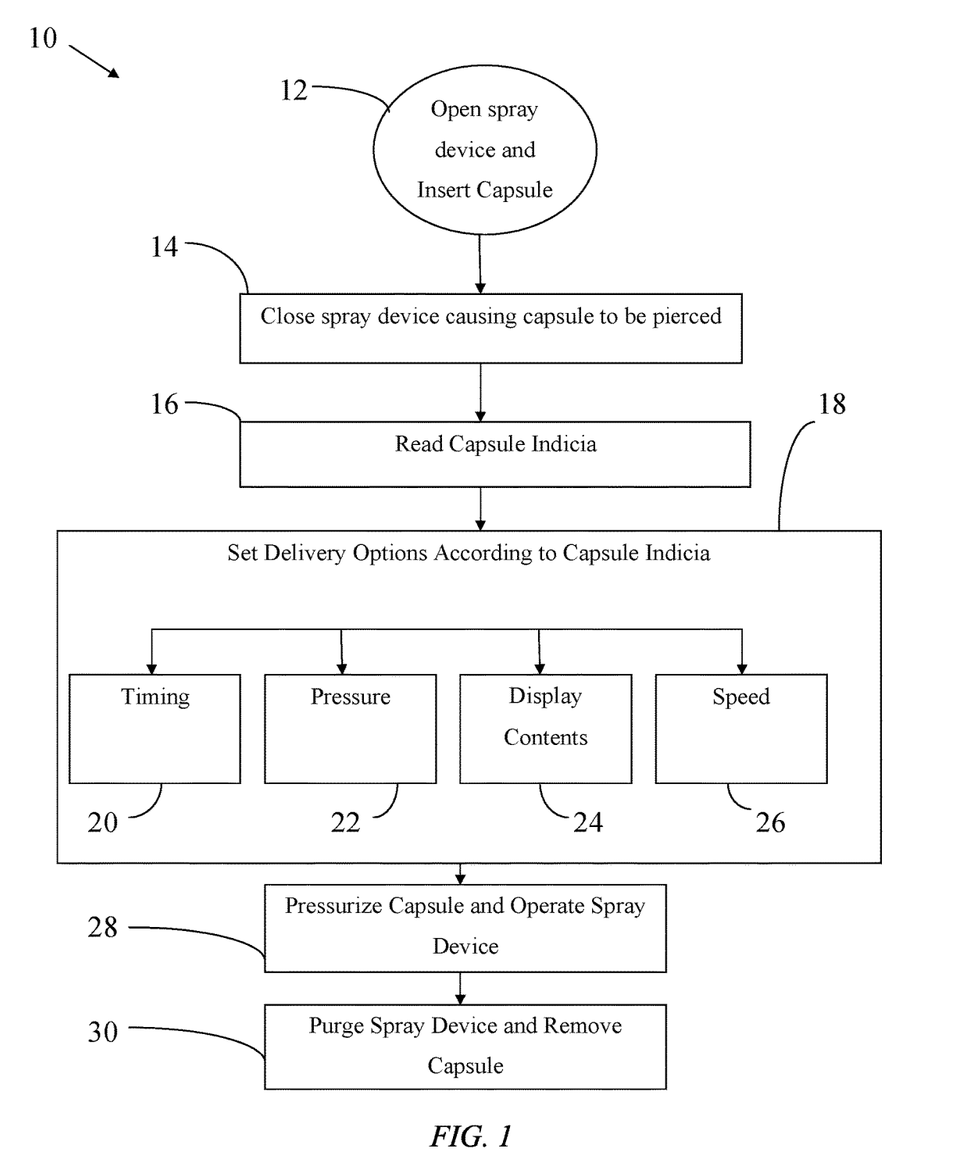
FIG. 1 is a flow chart of a method in accordance with the present invention.

FIG. 1 shows a method of using a dermal spray device in accordance with the present invention. The method is generally designated with the reference numeral 10. The step 12 includes opening the dermal spray device and inserting the capsule. The capsule includes a formulated fluid having a viscosity within a range appropriate for delivery to the skin of the subject using the device. The capsule may contain any of a variety of formulated fluids, each with its own unique fluid flow characteristics, so the device adapts to the formulated fluid in the capsule to optimize delivery of the formulated fluid.

The capsule, in one embodiment of the invention, is a generally cylindrical shape, having a generally cylindrical body with hemispherical ends. The hemispherical ends mechanically lock with the cylindrical body in one embodiment of the invention. In another embodiment of the invention, the hemispherical ends press fit with the cylindrical body. In yet another embodiment of the invention, the hemispherical ends adhere to the cylindrical body.

The capsule is sealed, to hold the formulated fluid. The step 14 closes the device causing the capsule be pierced. In one embodiment of the invention the device includes a door and defines a compartment for holding the capsule. The compartment includes at least one needle protruding from the compartment in a fixed orientation. Movement of the door from an open configuration to a closed configuration causes the capsule to be pierced by the needle. The device is closed when the doors in the closed configuration.

In one embodiment of the invention, the capsule includes readable indicia on the surface of the capsule. Readable indicia can be written language, numerical code, a barcode, a RFID tag or other indicia suitable for electronic reading. The step 16 reads the capsule indicia after the device is closed.

In a variation of the embodiment having a capsule with readable indicia, the device is equipped with appropriate hardware, software, and firmware to operate the device. After the step 16, the device sets various delivery options based on data collected from the step 16. Various parameters including timing 20, pressure 22, and speed 26 are determined. In one embodiment of the invention the device is equipped with an LED display to display various parameters of the indicia, and thus characteristics of the formulated fluid within the capsule. These various parameters may include initial volume, current volume, and ingredients of the formulated fluid. Pressure and flow rate of delivery are also parameters of the indicia. It can be appreciated that the fluid flow parameters can also be determined by the indicia.

The capsule readable indicia may also include various fluid properties including viscosity. From the readable indicia the device determines an appropriate pressure and speed of delivery on a volume per second basis for the formulated fluid enclosed within the capsule. In one embodiment the delivery settings are automatic, but it can be appreciated that the present invention can be adapted to offer the LED display various custom settings.

The step 28 of operating the device is initiated by a user. Operation can be initiated by providing the device button operable by the user to selectively initiate, pause and terminate operation of the device. In response to actuating the device button, the pump operates and pressurizes the capsule. In an alternate embodiment, the pump operates and creates a negative pressure in the device to draw formulated fluid from the capsule.

The device may have a period of latency when the pressure of the pump builds. The display, or light, or other indicator can inform a user when the device is ready to operate.

When operations are complete, the step 30 purges the device of any residual formulated fluid, opens the door the device and releases the capsule for removal. In one embodiment, opening the door automatically ejects the capsule. In another embodiment opening the door reveals a capsule for removal by the user. The step 30 of purging the device includes pumping air through the device to remove any residual formulated fluid.

Figure 2:
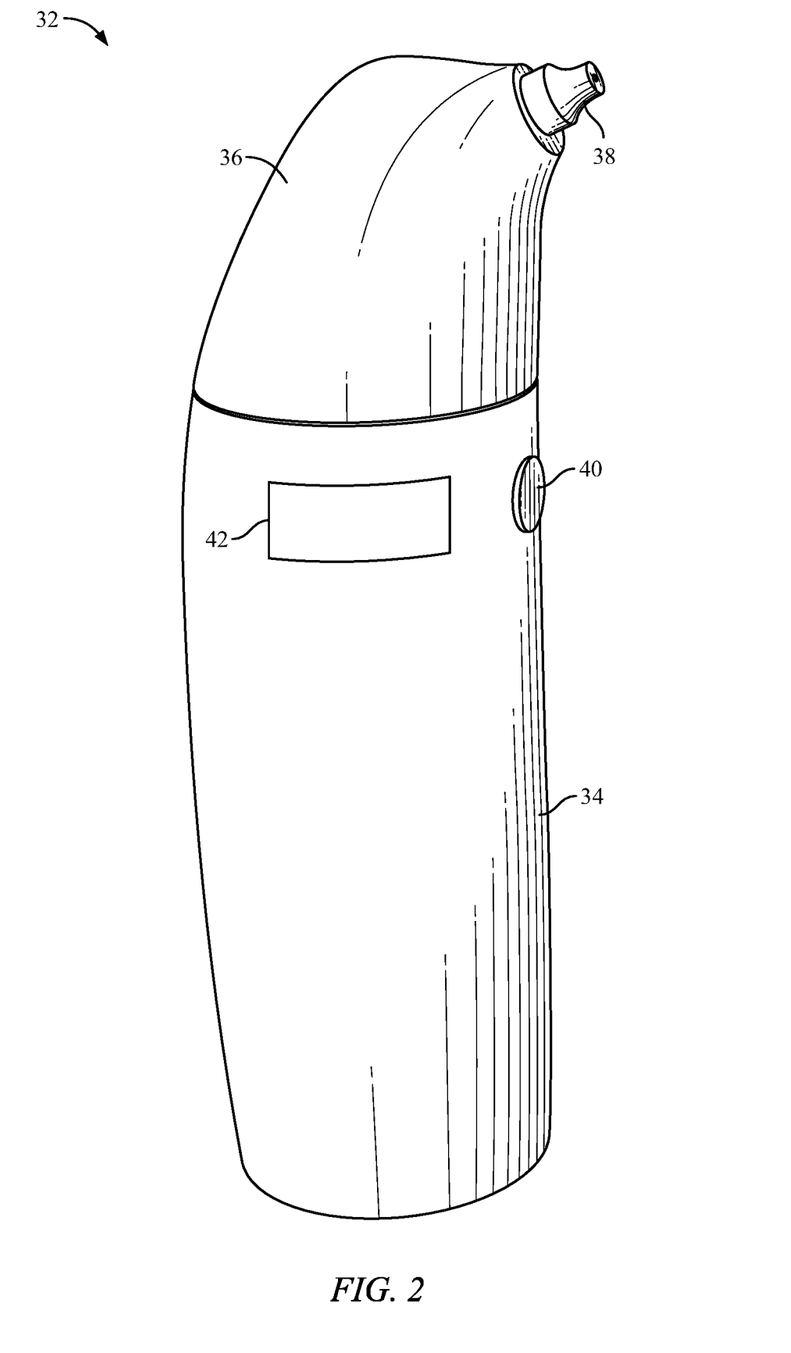
FIG. 2 is a perspective view of a dermal spray device in accordance with the present invention.

FIG. 2 shows a dermal spray device generally designated with the reference numeral 32. The device 32 includes a body 34, a spray head 36 and a nozzle 38. The body 34 includes a button 40 and a display 42 mounted on the body 34.

The device 32 is configured to be hand-held and may be contoured to accommodate the hand of a user for self-application, or for the hand of a user for application to another person. A variation of the device 32 includes a spray head 36 that rotatably mounts on the body and swivels with respect to the body 34 of the device 32. The button 40 extends through the surface of the body 34 to create a seal to inhibit dust, fluids and other material from penetrating the device 32. The display 42 is optional, and may include a LED screen to display operating parameters of the device 32, including identification of a particular formulated fluid contained within the device 32.

The nozzle 38 removeably mounts on the spray head 36. In one embodiment the nozzle 38 is adjustable to reduce or enlarge a spray pattern diameter. In another embodiment, the nozzle 38 is rotatably adjustable to modify the spray pattern. In a variation of this embodiment, the nozzle 38 is removable to enable replacement of nozzle 38 with an alternate nozzle having a different spray pattern. Nozzle 38 size and configuration suggestions can be listed by the indicia and published to the display 42, along with other instructions.

One benefit of the device 32 is that various formulated fluids can be utilized, where each has a unique viscosity and other fluid characteristics, and that a user need only press the button 40 to enable the device 32 to determine the fluid characteristics of the formulated fluid and spray the formulated fluid in an optimal way.

In one embodiment, the spray head 36 is affixed to the body 36 and seals to inhibit moisture and dust from penetrating the device 32. In another embodiment, the spray head 36 rotatably attaches to the body 34 to ergonomically align the nozzle 38 with the body 34.

Figure 3:
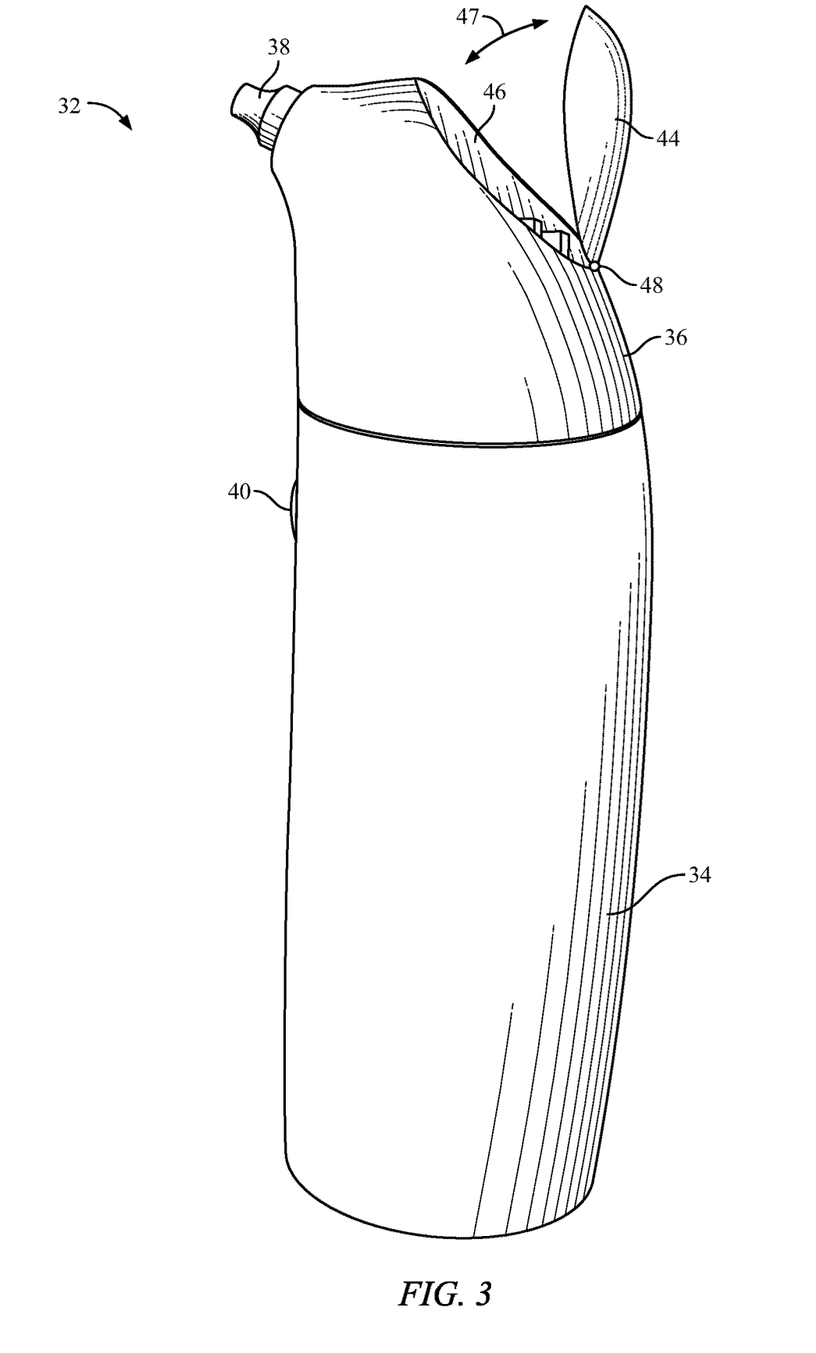
FIG. 3 is a perspective view of a dermal spray device with an open capsule door in accordance with the present invention.

FIG. 3 shows a perspective view of the device 32 showing the spray head 36 defining a compartment 46 and having a door 44 for selectively sealing the compartment 46. The door 44 includes a hinge 48 that attaches to the spray head 36 to selectively move from an open configuration as shown, to a closed configuration in the directions of the arrows 47.

In the closed configuration the door 44 lies in a flush-mount to with the surface of the spray head 36. In the closed configuration the door 44 seals against the spray head 36. Although a hinge 48 is used, it can be appreciated that a hook, latch, or other mechanical device for removeably holding the door 44 on the spray head 36 can be employed in accordance with the present invention.

Figure 4:
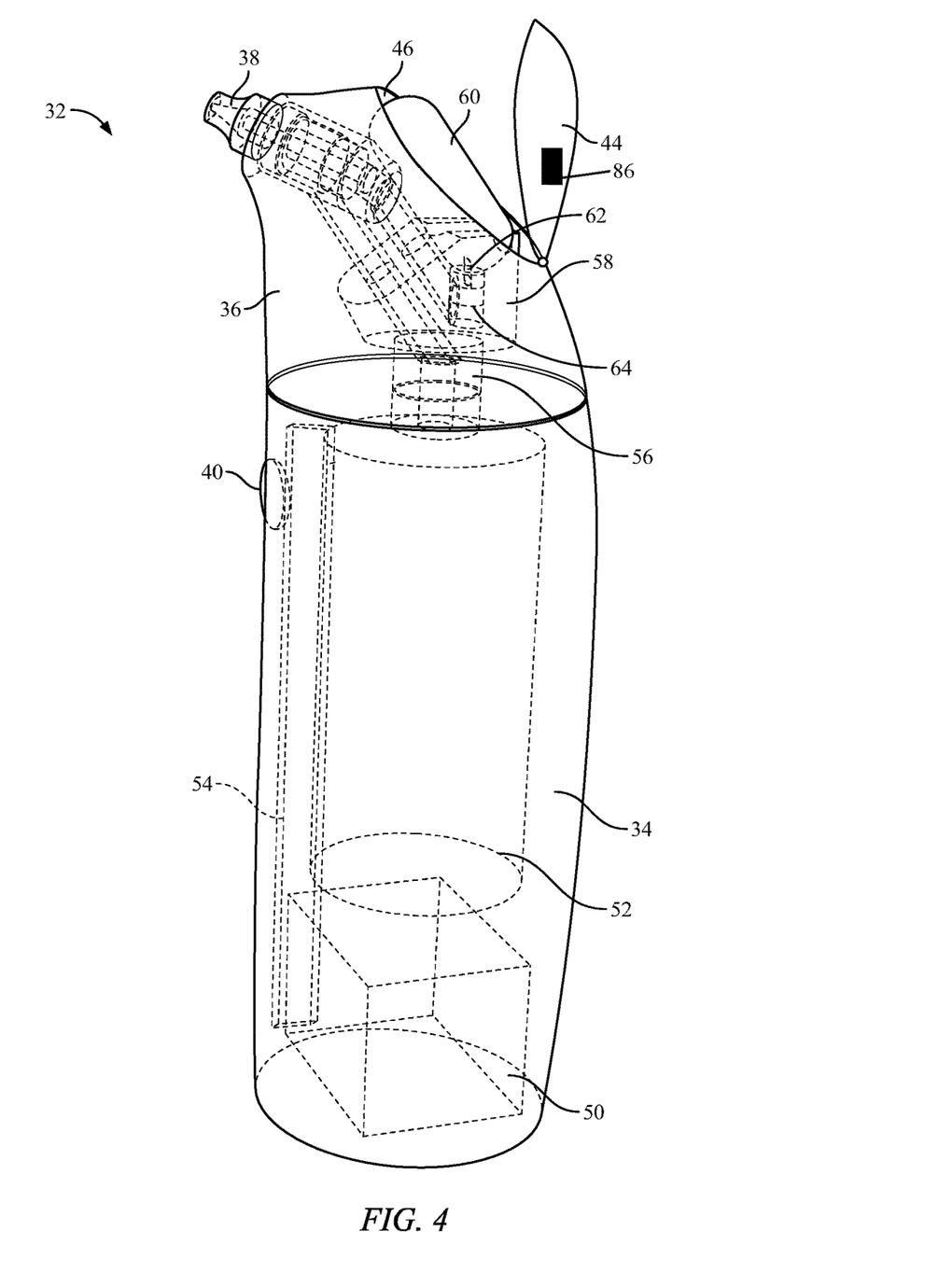
FIG. 4 is a perspective view of an embodiment of the present invention including hidden lines.

FIG. 4 shows the device 32 using hidden lines to reveal the internal components of the device 32. The door 44 is in an open configuration exposing the compartment 46. A capsule 60 is positioned within the compartment 60. Movement of the door 44 from the open configuration to a closed configuration seals the capsule within the spray head 36 of the device 32.

The device 32 includes a battery 50, an air compressor 52 and control circuitry 54, all in operative connection with each other and with the button 40. One end of the compressor 52 connects with the spray head 36. The compressor 52 connects with a pressurized conduit 36 defined within the spray head 36. The conduit 36 in turn connects with a capsule nest 58 defined within the spray head 36. The capsule nest 58 forms a portion of the compartment 46.

Preferably the battery 50 is a rechargeable battery having a loop coil to enable inductive charging. The batter 50 is a lithium ion battery in one embodiment of the invention. The compressor 52 operates on direct current from the battery 50. The battery 50 can be charged by placement of the device 32 into an inductive charging base so that a wireless connection is possible for recharging.

The compartment 46 is configured to hold a capsule containing the formulated fluid. It can be appreciated that the compartment 46 can be configured to hold a capsule of a variety of shapes and sizes. In one embodiment, the capsule is an ampoule manufactured from a plastic material. The compartment 46 has an appropriate volume and shape for receiving and holding a formulated fluid to be sprayed. The nest 58 is configured to hold the capsule 60 in a press fit in cooperation with the door. The nest 58 holds at least one needle 62. The needle 62 pierces the capsule to access fluid contain therein. The needle 62 is a hollow bore needle to establish fluid communication between the capsule 60 and the nozzle 38. In one embodiment, the needle includes a unidirectional valve in communication with the hollow bore. In another embodiment, the capsule 60 includes a membrane formed by scoring the surface of the capsule 60 in appropriate locations.

The use of a capsule 60 eliminates the need for a fluid coupling connection to an externally mounted compressor or pump. This makes precise operation of the device easier due to the lack of a tube or wire extending from the device. The capsule 60 is disposable and easily replaceable with virtually no mess. This makes purging and cleaning the device for use with alternate fluids very efficient. The use of a capsule 60 enables the interchanging of various fluid products in a rapid and efficient manner. The indicia on the capsule assure that both the device and the user know which fluid is being delivered, thus achieving a high degree of integrity. During the application of a formulated fluid, after a first fluid is applied, switching the device to a second fluid is easily achievable to save time. In one embodiment, the capsule (or a portion thereof) is colored-coded to enable rapid selection of desirable capsule contents. In this way, for example, a sunscreen can be applied after applying vitamin water, highlighter or other skin product.

The nest 58 defines a pressure chamber 64 in fluid communication with the conduit 56 and the pump 52. In one embodiment of the invention, compressed air from the pump 52 passes through the conduit 56 to the nozzle 38 and causes a negative pressure in the pressure chamber 64 by action of the Venturi Effect. This negative pressure draws fluid from the capsule 60 via the needle 62 and the pressure chamber 64 to be delivered through the nozzle 38. The fluid and the compressed air from the pump combine into a spray that is regulated by the nozzle 38.

In another embodiment, the needle 62 provides positive pressure directly into the capsule 60 and compressed air to the nozzle 38. A second needle mounted in the nest penetrates the capsule 60 to deliver pressurized fluid from the capsule to the nozzle 38 where it combines with compressed air and sprays out from the nozzle 38.

The pressure in the capsule 60 and the pressure of compressed air in the nozzle are optimized to yield optimal particle sizes of the fluid to yield a mist.

The control circuitry 54 includes a controller, a data table and an indicia reader 86 all in operative communication with each other. The indicia reader 86 mounts on the door 44 and communicates with the control circuitry 54 controller to read machine readable indicia from the capsule 60 when the capsule 60 is in the compartment 46 and the door 44 is closed.

In one embodiment of the invention, the indicia reader 86 is a radio frequency identification (RFID) tag reader and the capsule 60 includes a RFID tag attached to the capsule 60 surface. In another embodiment of the invention, the indicia reader 86 is an optical reader, and the capsule 60 includes a bar code. In yet another embodiment of the invention, the indicia reader 86 is an optical reader, and the capsule 60 includes machine readable text.

Figure 5:
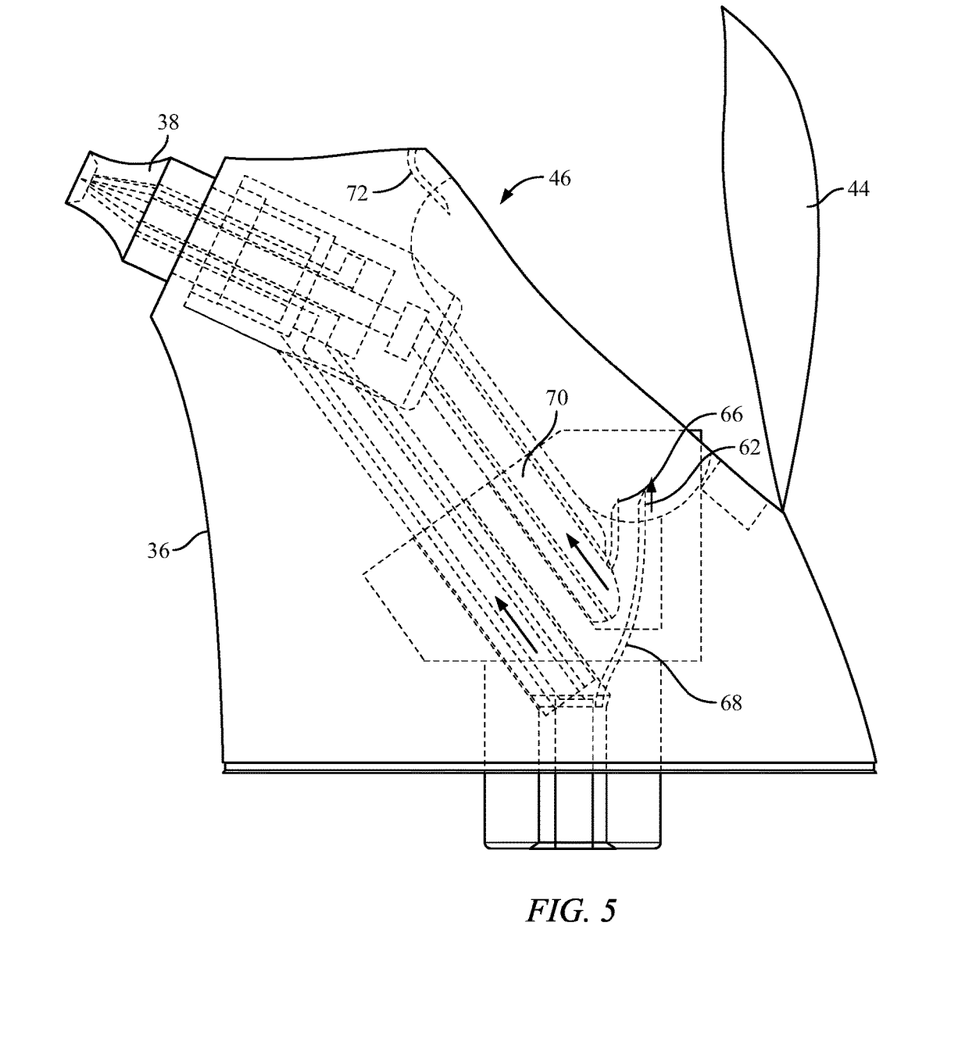
FIG. 5 is a side view of an embodiment of the spray head of the present invention including hidden lines.

FIG. 5 shows a side view of the spray head 36. The door 44 is in the open configuration exposing the compartment 46. The compartment 46 includes two needles 62 and 66, which are hollow bore needles having sharpened tips that extend to within the compartment 46. In one embodiment the needles 62 and 66 are fixed within the compartment 46.

It can be appreciated that the needles 62 and 66 can be axially moveable in response to the control circuitry 54 detecting movement of the door 44 into a closed configuration. Axial movement of the needles 62 and 66 can optimize insertion into, and penetration of, the capsule 60.

The needle 62 attaches in fluid communication with a conduit 68. The conduit 68 communicates in fluid communication with the pump 52 to deliver pressurized or compressed air through the needle 62 to pressurize the capsule 60 in the compartment 46. The needle 66 is in fluid communication with the nozzle 38 via a delivery conduit 70 to deliver fluid from the capsule 60 through the nozzle 38.

Figure 6:
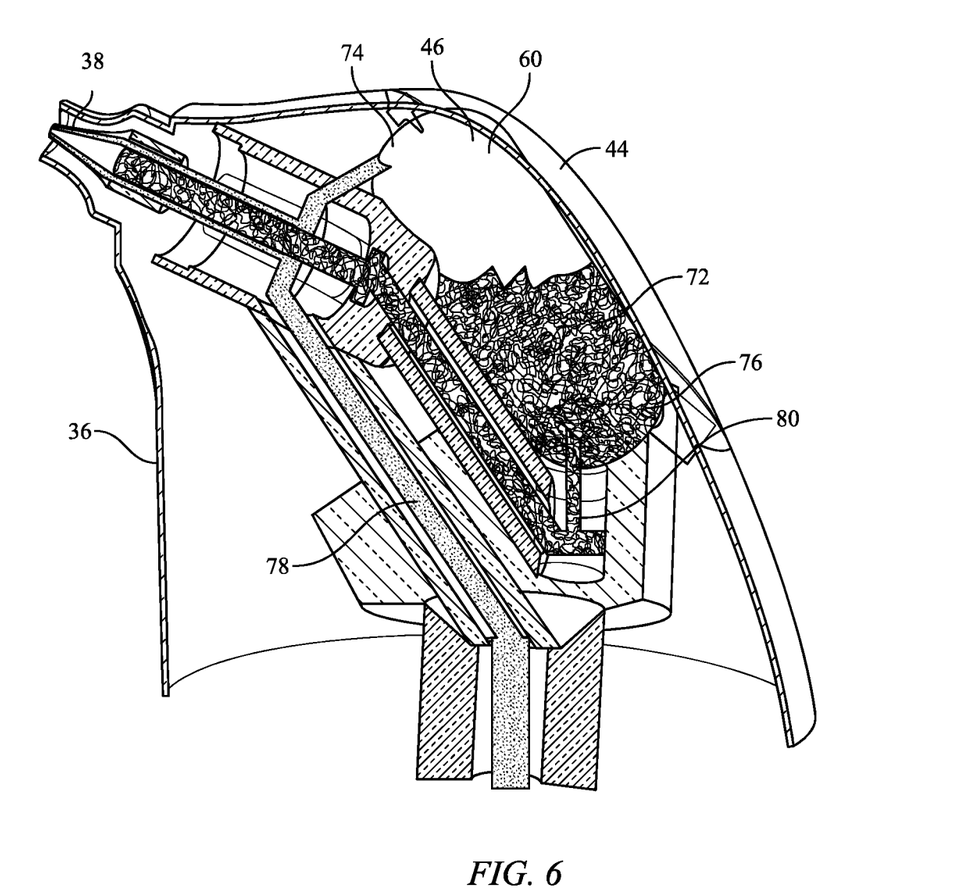
FIG. 6 is a cross-sectional view of an embodiment of the spray head of the present invention including hidden lines.

Optionally a third needle 72 extends into the compartment 46 to function as a pressure relief mechanism. The third needle 72 may include a check valve. The needle 72 allows ambient air at standard temperature and pressure to enter the capsule 60 so that the capsule does not deform, or improve delivery of the fluid within the capsule FIG. 6 is a cross-sectional view of the spray head 36. The compartment 46 includes a capsule 60 that holds fluid 72. Preferably the fluid 72 is a formulated fluid such as, for example, a skin care product, a cosmeceutical, a transdermal nutraceutical, make up, insect repellent, or sunscreen product.

The capsule 60 has an upper end 74 and a lower end 76. A conduit 78 is defined within the spray head to deliver compressed air from the pump to the capsule 60 at the top end 74 through a needle. A conduit 80 at the bottom end 76 of the capsule is defined within the spray head 36 to deliver fluid 72 through the nozzle 38.

The door 44 is in a closed configuration to hold the capsule 60 within the spray head 36 and to establish fluid communication between the capsule 60 and the conduits 80 and 78.

Figure 7:
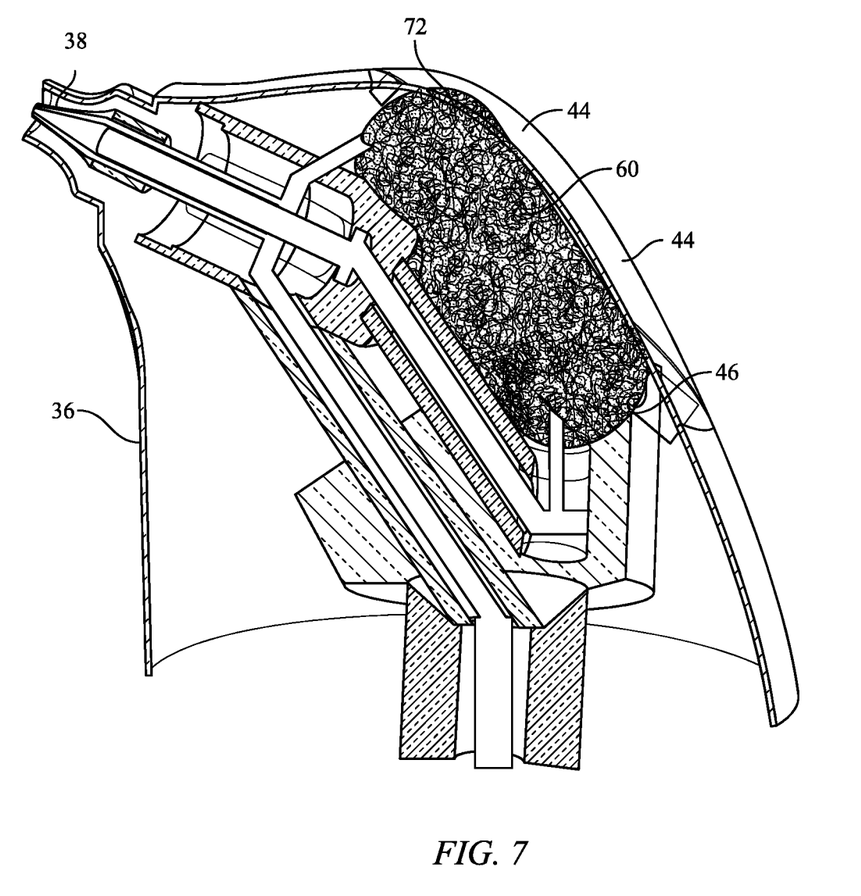
FIG. 7 is a cross-sectional view of an embodiment of the spray head of the present invention having a full capsule.

FIG. 7 is a cross-sectional view of the spray head 36 after a capsule is inserted into the compartment 46. The door 44 is in the closed configuration. The capsule 60 is full of fluid 72. The button 40 (FIG. 2) selectively initiates delivery of fluid from the capsule through the nozzle 38.

Figure 8:
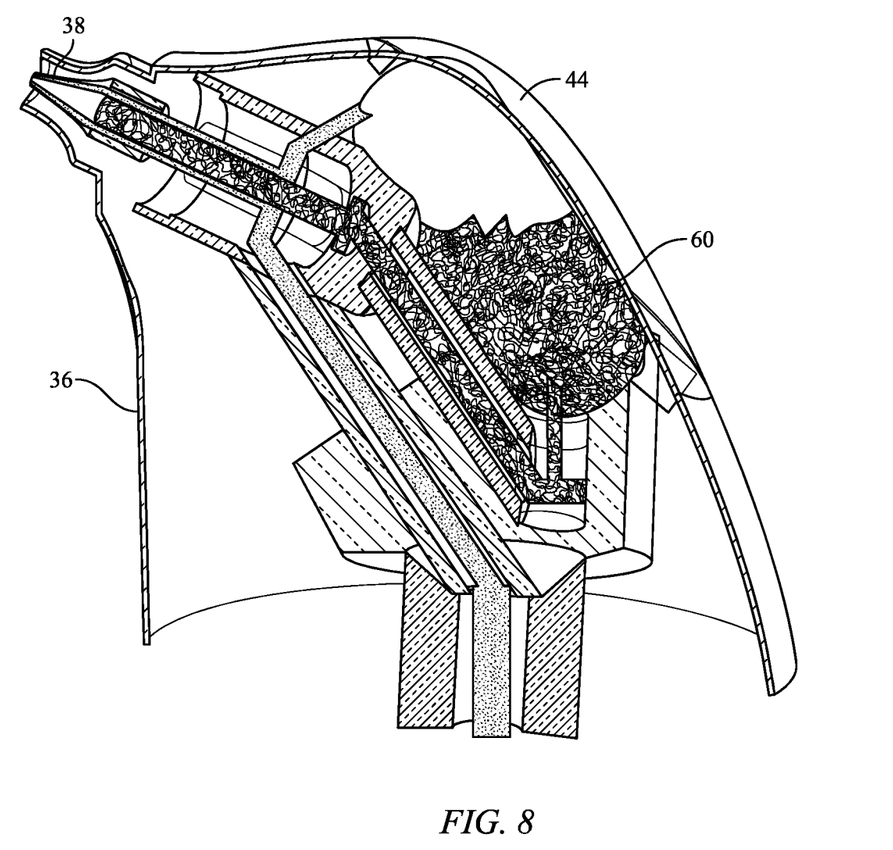
FIG. 8 is a cross-sectional view of an embodiment of the spray head of the present invention having a partially full capsule.

FIG. 8 is a cross-sectional view of the spray head 36 after a capsule is inserted into the compartment 46 and the pump (FIG. 2) is actuated by the button 40 (FIG. 2). The capsule 60 dispenses fluid 72 and eventually empties. As shown the capsule 60 is partially empty.

After the capsule 60 is emptied, the door 44 is opened and the capsule is removed. The various fluid conduits can be flushed by activating the pump to push compressed air through the spray head. Additionally, a new capsule 60 is introduced via the door 44. The operation of the device continues with the insertion of the new capsule 60.

Figure 9:
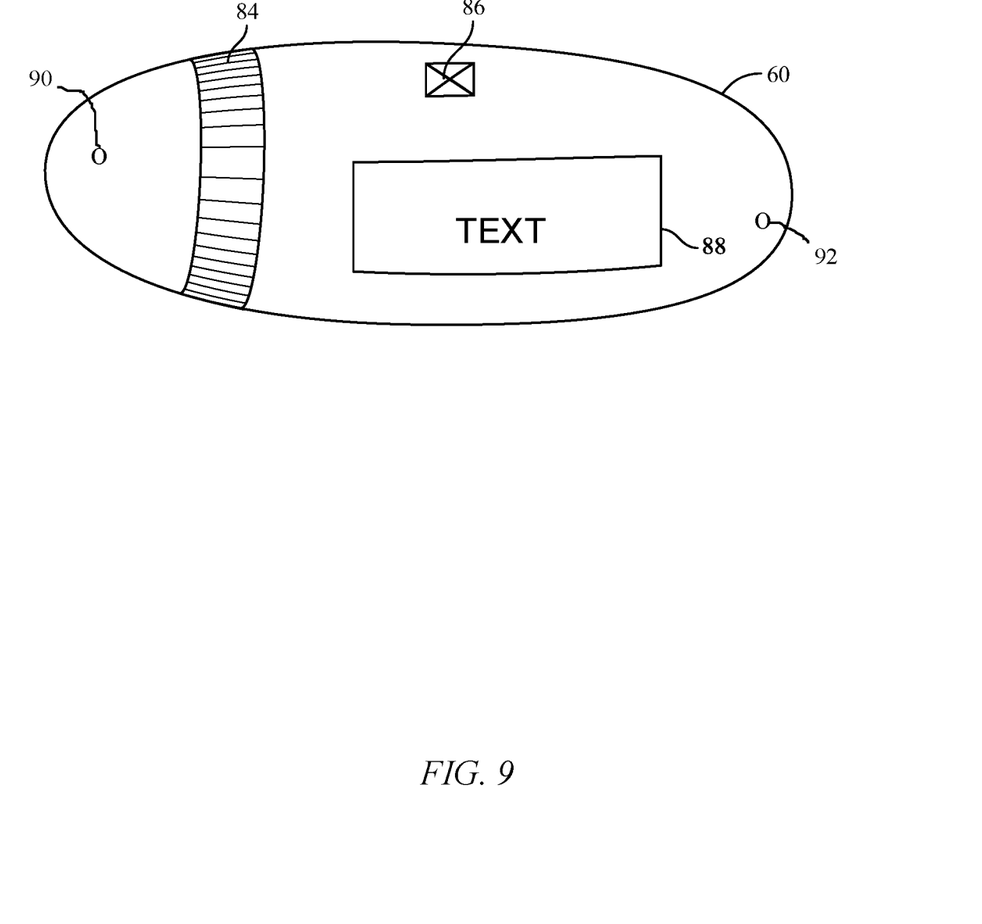
FIG. 9 is a side perspective view of a capsule in accordance with the present invention.

FIG. 9 shows a capsule 60. The capsule 60 has a surface including machine readable indicia. The capsule 60 in one embodiment includes one or more of text 82, a bar code 84, a radio frequency identification (RFID) device 86 to enable the device 32 to detect the capsule 60. In one embodiment the indicia wraps around the capsule as shown by the bar code 84 so that it can be read in any orientation. The RFID device 86 is also readable from any orientation at a particular distance range. The machine readable indicia are important to enable the device to properly pressurize and dispense the fluid enclosed in the capsule.

In one embodiment, selected data from the machine readable indicia are published on the display 42 to enable a user to determine the contents of the capsule 60 without opening the device.

Preferably the capsule 60 has a membrane 90 and 92 at each end to facilitate penetration of the capsule by a needle during use. The membrane can be a thinned portion of the capsule itself. For example, select zones of the capsule can be etched to reduce thickness and ease penetration by a hollow bore needle having a sharp end. Alternatively, the capsules 60 define openings at each end, and a membrane patch over each opening facilitates needle penetration. The membrane 90 and 92 need not be a fixed point, but may instead be scribed around the circumference of the capsule 60 so that alignment of the membrane with a needle can be assured. The membranes 90 and 92 seal the capsule 60 until the membranes are penetrated by needles.

Figure 10:
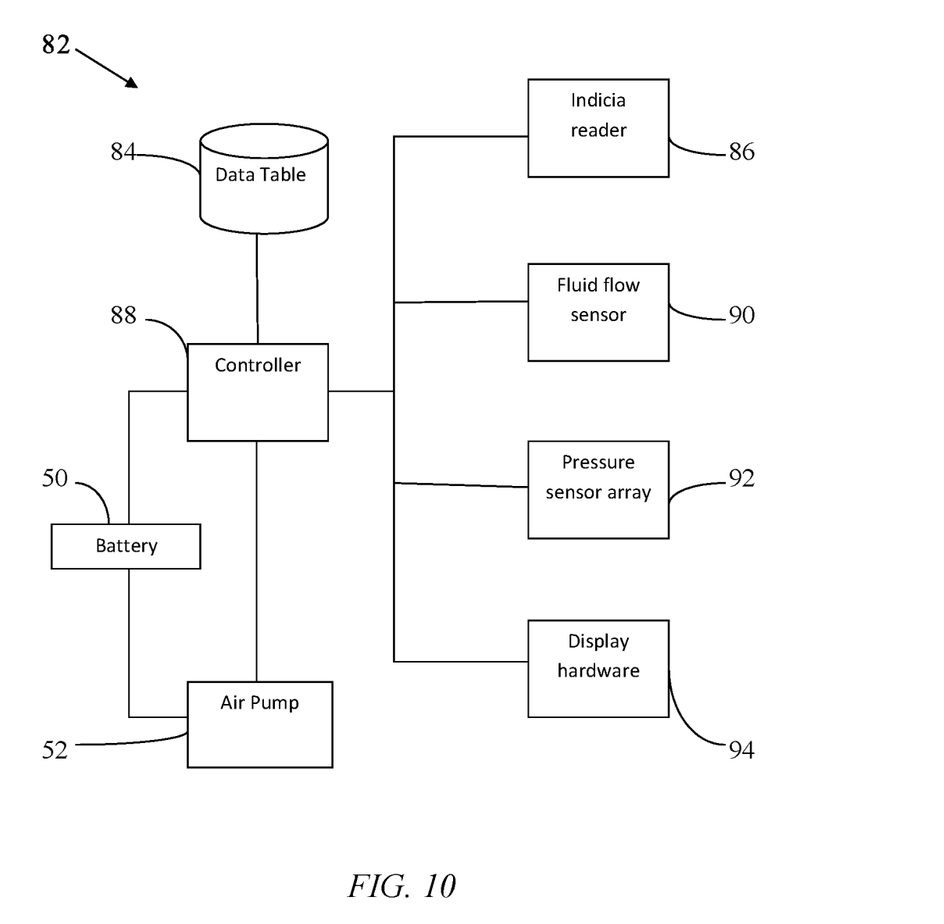
FIG. 10 is a system diagram in accordance with the present invention.

FIG. 10 is a control system in accordance with the present invention generally designated with the reference numeral 82. The control system 82 includes a data table 84, indicia reader 86, a controller 88, a fluid flow sensor 90, a pressure sensor array 92, and display hardware 94. The control system 82 operates with the battery 50 and the air pump 52.

Preferably the indicia reader is attached on or within the door 44 (FIG. 4) of the present invention.

The data table 88 is a table providing data that is accessed by the controller 88 in response to the indicia reader 86 reading machine readable indicia on a capsule inserted into a dermal spray device of the present invention. The data includes details regarding capsule contents such as a formulated cosmetic product, and the detailed viscosity, recommended operation pressure, and recommended fluid flow rate.

The fluid flow sensor 90 is in communication with the controller 88 to verify that the recommended fluid flow rates are achieved during operation in real time using closed control feedback loop.

The pressure sensor array 92 detects pressures in various points in the system 10 (FIG. 2). The points include at the pump, in the capsule, and in the nozzle.

The display hardware includes firmware including memory with instructions programmed to display portions of the data table 88 to a user. This data can include text identifying the contents of the capsule, and an indication of the volume on a percentage basis stored in the capsule. Additional information that is displayed by the display hardware includes battery life.

The controller 88 activates the air pump 52 in response to activating the button 40 (FIG. 2), and the air pump 52 is powered by the battery 50.

It can be appreciated that the subject can be human or other sentient life form. It can also be appreciated that the capsule described herein a generally cylindrical in shape, it can have any of a variety of shapes. Further, while the machine readable indicia described are simple examples, other machine readable indica, and corresponding hardware, can be used, such as ultrasonic devices, data matrix (2-D) bar codes and readers, color pattern readers, and even readers that detect optical characteristics beyond the visible light range.

It can also be appreciated that the present invention can be utilized to deliver potent nutraceutical to remedy various diseases that can be addressed by transdermal delivery systems. The present invention is particularly suited for delivering plant extracts, particularly, those that are formulated to be water soluble. The present invention enables a more uniform distribution over the skin surface so that a large skin surface can be affected by the formulated fluid. This larger surface area facilitates transdermal delivery of efficacious substances including specific cannabinoids, and whole plant extracts. The present invention can be used to treat various types of skin cancers, for example.

The control system can be programmed to regulate dosage of the transdermal delivery of various nutraceutical and cosmeceutical formulated fluids. Other uses of the present invention include topical vitamin and mineral applications to the skin of a subject, remedies for muscular pain, remedies for inflammation, cellulite reduction and breast finning.

We claim:

1. A dermal spray device, comprising
    a body enclosing a battery, a pump and control electronics operatively connecting the battery and the pump;
    a spray head rotatably mounted on the body, the spray head including a spray nozzle and defining a compartment for receiving a capsule containing formulated fluid;
    a first needle attached within the compartment to pierce a capsule in the compartment, the first needle being in fluid communication with the pump;
    a second needle attached within the compartment to pierce a capsule in the compartment, the second needle being in fluid communication with the nozzle;
    a display and a fluid flow sensor, the display indicates the formulated fluid and the fluid flow during operation;
    a door mounted on body to selectively open and close the compartment to enable rapid insertion and removal of the capsule therein; and
    whereby, when a capsule inserts into the compartment, the needles pierce the capsule and the pump pressurizes the inserted capsule to spray the fluid through the nozzle,
    the device further comprising control circuitry mounted within the device, the control circuitry includes a controller, a data table and an indicia reader all in operative communication with each other,
    wherein the controller includes a feedback loop to regulate fluid flow during operation;
    wherein the indicia reader is mounted on the door to read machine readable indicia from the capsule when the capsule is in the compartment and the door is closed;
    wherein the indicia reader is a radio frequency identification (RFID) tag reader and the capsule includes a RFID tag.

2. The device as set forth in claim 1, wherein the indicia reader is an optical reader, and the capsule includes a bar code.

3. The device as set forth in claim 1, wherein the indicia reader is an optical reader, and the capsule includes machine readable text.

* * * * *